US011478356B2

(12) United States Patent
Daniel et al.

(10) Patent No.: US 11,478,356 B2
(45) Date of Patent: Oct. 25, 2022

(54) HELICAL GRAFT CONTAINMENT CAGE

(71) Applicant: DePuy Synthes Products, Inc., Raynham, MA (US)

(72) Inventors: Steffan Daniel, Zuchwil (CH); André Furrer, Zuchwil (CH); Scott Larsen, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1128 days.

(21) Appl. No.: 15/411,499

(22) Filed: Jan. 20, 2017

(65) Prior Publication Data
US 2017/0216034 A1    Aug. 3, 2017

Related U.S. Application Data

(60) Provisional application No. 62/288,273, filed on Jan. 28, 2016.

(51) Int. Cl.
*A61F 2/28* (2006.01)
*A61F 2/30* (2006.01)

(52) U.S. Cl.
CPC .......... *A61F 2/2846* (2013.01); *A61F 2/2803* (2013.01); *A61F 2002/285* (2013.01); *A61F 2002/2835* (2013.01); *A61F 2002/30289* (2013.01); *A61F 2002/30403* (2013.01); *A61F 2002/30471* (2013.01); *A61F 2002/30578* (2013.01)

(58) Field of Classification Search
CPC ........ A61F 2/2803; A61F 2/4846; A61F 2/28; A61F 2002/2807; A61F 2002/2835; A61F 2002/285; A61F 2002/30289; A61F 2002/30291; A61B 17/8085
See application file for complete search history.

(56) References Cited

U.S. PATENT DOCUMENTS

| 4,787,906 | A | 11/1988 | Haris |
| 6,149,651 | A | 11/2000 | Drewry et al. |
| 6,280,473 | B1 * | 8/2001 | Lemperle ............. A61B 17/688 128/898 |
| 6,447,543 | B1 * | 9/2002 | Studer .................. A61F 2/4455 623/17.11 |
| 6,989,033 | B1 * | 1/2006 | Schmidt ................... A61F 2/44 623/23.51 |
| 2005/0234557 | A1 * | 10/2005 | Lambrecht ........... A61B 5/1076 623/17.16 |

(Continued)

FOREIGN PATENT DOCUMENTS

| CN | 101027016 | 8/2007 |
| DE | 44 09 836 | 9/1995 |

(Continued)

*Primary Examiner* — Matthew J Lawson
(74) *Attorney, Agent, or Firm* — Fay Kaplun & Marcin, LLP (57) ABSTRACT

A bone graft containment device includes a body formed via one or more helical structures extending about a longitudinal axis of the body from a first end to a second end to define a channel extending longitudinally therethrough. The channel is configured to receive a bone graft or bone graft substitute material therein, the one or more helical structures formed of a material permitting the body to be one of expanded, compressed and curved to fill a target space of a target bone.

23 Claims, 7 Drawing Sheets

(56) References Cited

U.S. PATENT DOCUMENTS

| | | | |
|---|---|---|---|
| 2005/0273165 A1* | 12/2005 | Griffiths | A61C 8/0006 623/16.11 |
| 2013/0164707 A1* | 6/2013 | Ali | A61C 8/0027 433/173 |
| 2013/0325129 A1* | 12/2013 | Huang | A61F 2/44 623/17.16 |
| 2015/0051876 A1 | 2/2015 | Rueber et al. | |
| 2016/0220289 A1* | 8/2016 | Taras | A61B 17/8085 |
| 2016/0277844 A1* | 9/2016 | Kopetz | H04R 3/00 |
| 2016/0287391 A1* | 10/2016 | Larsen | A61F 2/2846 |
| 2016/0324656 A1* | 11/2016 | Morris | A61F 2/30744 |
| 2017/0231767 A1* | 8/2017 | Larsen | A61F 2/2846 623/23.58 |
| 2018/0193530 A1 | 7/2018 | Barbas et al. | |
| 2018/0221153 A1* | 8/2018 | Daniel | A61F 2/28 |
| 2018/0368981 A1* | 12/2018 | Mattes | A61L 27/045 |
| 2019/0076251 A1* | 3/2019 | Daniel | A61F 2/2803 |
| 2019/0076252 A1* | 3/2019 | Karg | A61F 2/2803 |

FOREIGN PATENT DOCUMENTS

| | | |
|---|---|---|
| JP | 2003165761 | 6/2003 |
| JP | 2015503943 | 2/2015 |

* cited by examiner

HELICAL GRAFT CONTAINMENT CAGE

PRIORITY CLAIM

The present application is a Non-Provisional Application which claims priority to U.S. Provisional Patent Application Ser. No. 62/288,273 filed on Jan. 28, 2016. The specification of the above-identified application is expressly incorporated herein by reference.

BACKGROUND

Mandible defects are often treated with bone grafts and/or implants such as, bone plates, to assist with healing. The bone grafts may be placed in the target area using any of a variety of methods. However, without a container for the bone graft, the graft may fall away from a target site before it can be incorporated by the body into the bone.

SUMMARY

The present invention is directed to a bone graft containment device, comprising a body formed via one or more helical structures extending about a longitudinal axis of the body from a first end to a second end to define a channel extending longitudinally therethrough, the channel configured to receive a bone graft or bone graft substitute material therein, the one or more helical structures formed of a material permitting the body to be one of expanded, compressed and curved to fill a target space of a target bone.

The present invention is also directed to a bone graft system, comprising a graft containment device including a body formed via one or more helical structures extending about a longitudinal axis of the body from a first end to a second end to define a channel extending longitudinally therethrough, the channel configured to receive a bone graft material therein, the one or more helical structures fixated of a material permitting the body to be one of expanded, compressed and curved to fill a target space of a target bone, and a fixation plate sized and shaped to be positioned along a length of the graft containment device to attach the graft containment device to the bone, the attachment including openings extending therethrough for receiving fixation elements therethrough.

The present invention is also directed to a method for treating a bone, comprising inserting a bone graft material into a channel of a graft containment device, the graft containment device including a body formed via one or more helical structures extending about a longitudinal axis of the body from a first end to a second end to define the channel, and one of expanding, compressing and bending the graft containment device to fill a target space of a target mandible bone and positioning the graft containment device in the target space.

BRIEF DESCRIPTION

DETAILED DESCRIPTION

The present invention may be understood with reference to the following description and the appended drawings, wherein like elements are referred to with the same reference numerals. The present invention relates to the treatment of bone and, in particular, relates to treatments using bone grafts. Exemplary embodiments of the present invention describe a graft containment cage configured to be positioned in a gap or space formed in a bone (e.g., mandible) so that graft material may be packed therein to encourage and guide the generation of new bone within the space of the bone. The graft containment device of the exemplary embodiment is formed via a helical construction which allows for increased flexibility of individual struts of the device. This construction permits the graft containment device to be extended, compressed and/or curved to fit the space of the bone into which it is to be inserted. The graft containment device of one embodiment is sized, shaped and structured to treat defects of the mandible. Although the exemplary embodiment is shown and described as useful in treating a mandible, it will be understood by those of skill in the art that the graft containment device of the present invention may also be formed in different shapes and sizes to per unit its use in treating other types of bone which would benefit from the use of a graft containment device.

Figure 1:
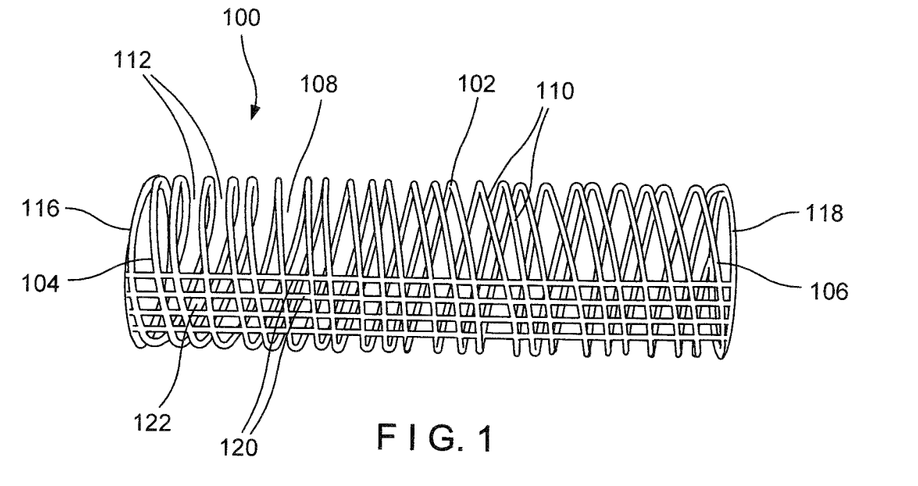
FIG. 1 shows a longitudinal side view of a device according to an exemplary embodiment of the present invention.
Figure 2:
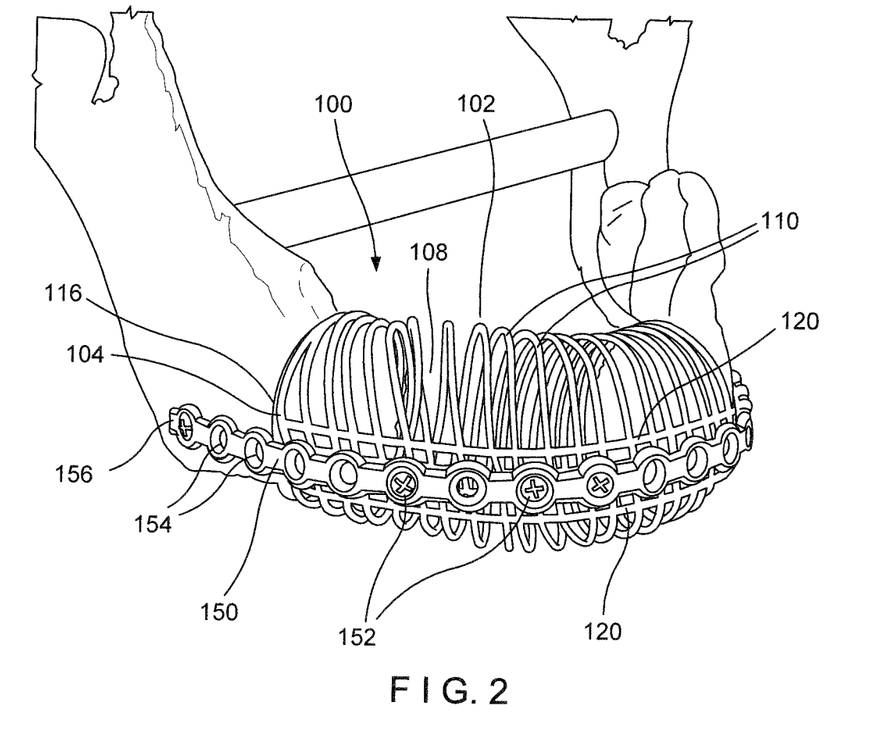
FIG. 2 shows a perspective view of the device of FIG. 1 in use with a fixation plate.
Figure 3:
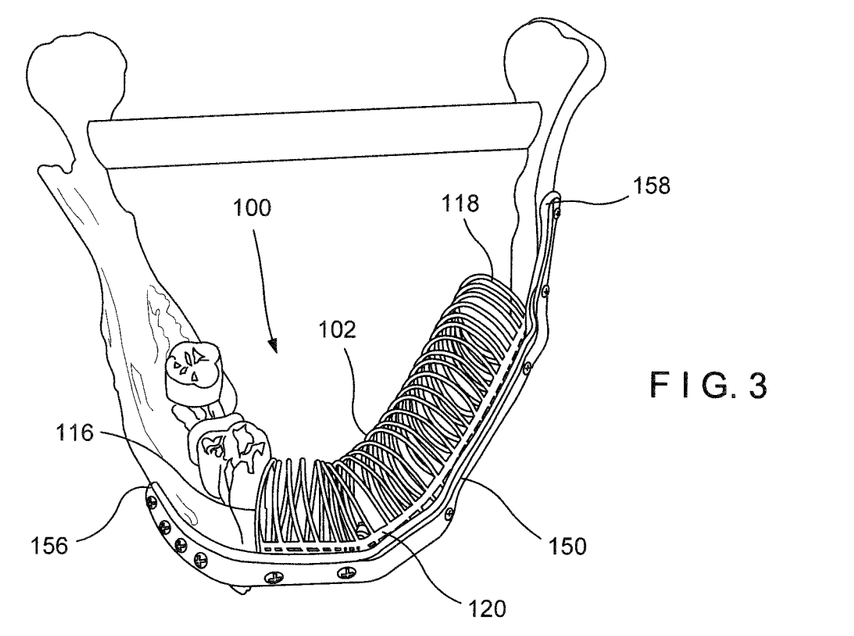
FIG. 3 shows another perspective view of the device of FIG. 1 in with the fixation plate.

As shown in FIGS. 1-3, a graft containment device 100 according to a first exemplary embodiment of the present invention comprises a body 102 extending longitudinally from a first end 104 to a second end 106 and including a channel 108 extending therethrough. The body 102 may be formed via at least one helical structure 110 extending from the first end 104 to the second end 106. Those skilled in the art will understand that the device may include multiple helical structures with a first one of the helical structures 110 extending along only a part of the length of the device 100 while a second structure 110 extends along all or part of the length of the device 100. The helical structure 110 is wrapped about a longitudinal axis of the device 100 to form a perimeter of the device 100. The structure 110 extends around the longitudinal axis of the device 100 in a generally helical configuration defining the channel 108. Those skilled in the art will understand that the helical configuration refers generally to the wrapping of the structure 110 about the longitudinal axis at an angle relative to planes perpendicular to the longitudinal axis while the shape of the perimeter of the device 100 need not be strictly helical as the shape of the perimeter will be defined to mimic as closely as possible the shape of a portion of bone which is to be replaced by the graft.

The body 102 of the graft containment device 100 is sized and shaped so that, when the graft containment device 100 is positioned in a target space or gap within a bone, the body 102 substantially matches an outer profile of the bone. In one exemplary embodiment, the body 102 is sized and shaped to be positioned between two separated portions of a target bone so that each of the ends 104, 106 substantially matches a profile of an outer surface of a corresponding one of the ends of the separated portions of bone. The helical structure 110 permits the graft containment device 100 to be longitudinally compressed or expanded and/or curved to extend along a path of a portion of bone to be replaced. Graft material may be inserted into the channel 108 via the open first and second ends 104, 106. Alternatively, or, in addition, graft material may be inserted into the channel 108 via a space 112 between adjacent turns of the helical structure 110 or, where the graft containment device 100 includes more than one helical structure 110, a space 112 between adjacent helical structures 110. As will be understood by those of skill in the art, the space 112 may be enlarged to facilitate insertion of the bone graft material by moving adjacent turns of the one or more helical structures 110 away from one another.

The body 102 of the graft containment device 100 extends longitudinally from the first end 104 to the second end 106 and generally defines a shape corresponding to the profile of the outer surface of the target bone—particularly the mandible. In the embodiment shown in FIGS. 1-3, the body 102 is formed via a plurality of helical structures 110, first ends 104 of the helical structures 110 being connected to one another via a first connecting structure 116 and second ends 106 of the helical structures 110 connected to one another via a second connecting structure 118. The helical structures 110 extend about the longitudinal axis of the graft containment device 110 to define the channel 108. In one embodiment, the body 102 may be substantially cylindrical and the first and second connecting structures 116, 118 may be configured as rings. It will be understood by those of skill in the art, however, that the body 102 along with the first and second connecting structures 116, 118 may have any of a variety of shapes to match an outer profile of the target space in which the graft containment device 100 is inserted. It will also be understood by those of skill in the art that the graft containment device 100 may be formed of a flexible material so that, even if the body 102 is not the exact shape of the target space which it is intended to fill, the graft containment device 100 may be flexed and deformed to fit the desired target space. For example, the graft containment device 100 may be formed of materials such as, Polycapralactone (PCL), Polylactide and/or Titanium.

Figure 4:
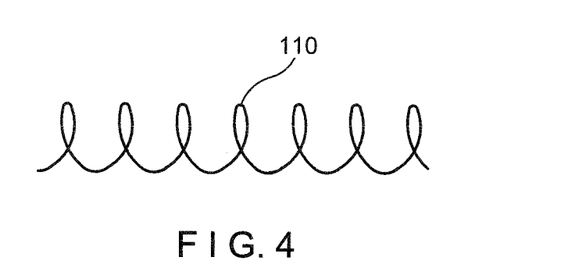
FIG. 4 shows longitudinal side view of a device according to another exemplary embodiment of the present invention.

Although FIGS. 1-3 show a graft containment device 100 formed of a plurality of helical structures 110, as described above, the graft containment device 100 may alternatively be formed from a single helical structure 110, as shown in FIG. 4. Where the graft containment device 100 includes only a single helical structure 110, first and second connecting structures 116, 118 are not required.

In a further embodiment, the graft containment device 100 may also include longitudinal struts 120 extending along at least a portion of a length of the body 102. The longitudinal struts 120 may be useful for strengthening and/or stiffening all or part of the body 102 and/or for the insertion of fixation elements 152. For example, the graft containment device 100 may be used in conjunction with a fixation plate 150 or other attachment, as shown in FIGS. 2 and 3, which may be used to align separated portions of bone. The fixation plate 150 may be fixed to the graft containment device 100 and to the separated portions of bone, to form a bridge maintaining the separated portions of bone and the device 100 in a target alignment. The fixation plate 150 may be fixed to the graft containment device 100 via screws inserted through an opening in the fixation plate and into a space 122 between adjacent longitudinal struts 120. The graft containment device 100 should therefore include at least two longitudinal struts 120. In one exemplary embodiment, the graft containment device 100 may include four longitudinal struts 120. It will be understood by those of skill in the art, however, that the graft containment device 100 may include any number of longitudinal struts 120. As would be understood by those skilled in the art, the struts 120 may be positioned as desired to aid in retaining the graft material within the device 100. For example, for certain applications in which a bone is generally oriented with one side facing downward (e.g., the mandible), the struts 120 may be placed along the bottom to prevent the migration of material out of the device 100 through the influence of gravity.

Figure 5:
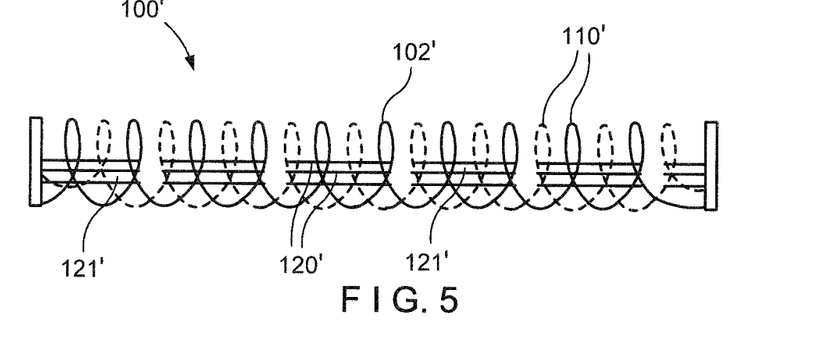
FIG. 5 shows a longitudinal side view of a device according to an alternate embodiment of the present invention.

In one exemplary embodiment, the longitudinal struts 120 extend along an entire length of the body 102. In this embodiment, the longitudinal struts 120 prevent a length of the graft containment device 100 from being expanded or compressed while permitting the body 102 to be bent or flexed relative to the longitudinal axis. In another exemplary embodiment, as shown in FIG. 5, longitudinal struts 120' may be interrupted along a length of a body 102' of a graft containment device 100' so that the device 100' includes multiple sets 121' of longitudinal struts 120' along a length of the body 102'. Longitudinal struts 120' of each set 121' extend along a plurality of adjacent turns of one or more helical structures 110' and are separated from longitudinal struts 120' of an adjacent set 121' by a plurality of adjacent turns of the one or more helical structures 110'. The interrupted longitudinal struts 120' allows for extension and/or compression of the graft containment device 100' at specific locations along a length of the body 102'. In particular, the body 102' may be expanded and/or compressed at portions of the body 102' which do not include the longitudinal struts 120'—i.e., where the sets 121' of longitudinal struts 120' are separated from one another.

Figure 6:
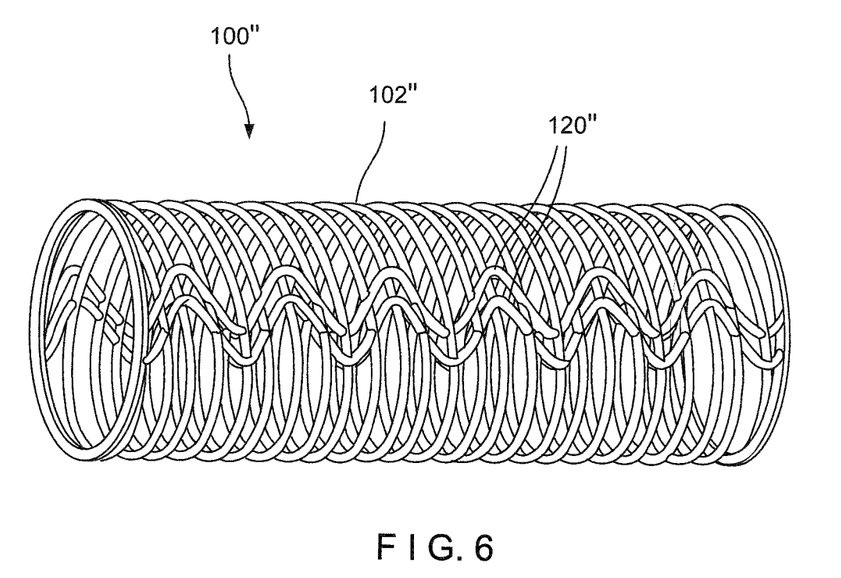
FIG. 6 shows a perspective view of a device according another alternate embodiment of the present invention.
Figure 7:
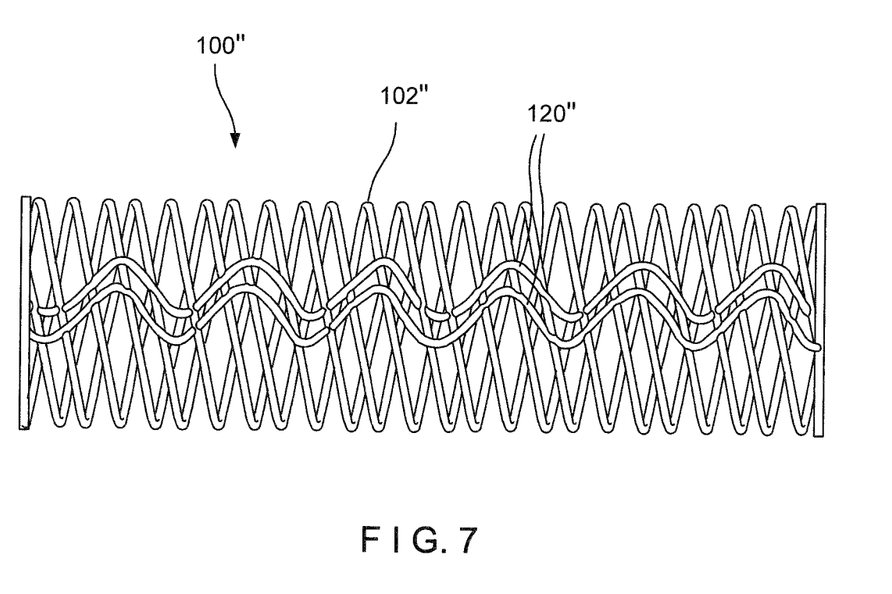
FIG. 7 shows a longitudinal side view of the device of FIG. 6.
Figure 8:
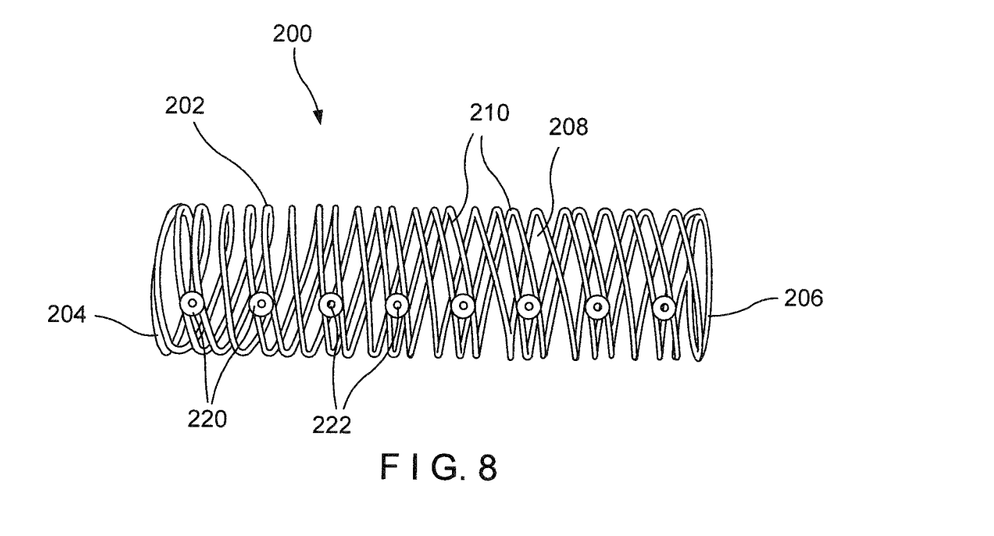
FIG. 8 shows a longitudinal side view of a device according to another exemplary embodiment of the present invention.

Although the devices 100, 100' show the longitudinal struts 120, 120', respectively, as extending substantially linearly (e.g., along a substantially straight line) along at least a portion of a length of the body 102, 102', it will be understood by those of skill in the art that struts may extend longitudinally along at least a portion of a length of the body in any of a number of configurations. For example, according to another exemplary embodiment, as shown in FIGS. 6 and 7, a body 102" of a graft containment device 100", which may be substantially similar to the devices 100, 100' described above, may include a plurality of struts 120" extending longitudinally along the body 102" in an oscillating wave (e.g., sinusoidal) configuration. The wave configuration of the struts 120" strengthens the body 102" while also allowing flexibility of the body 102" in all axes. Thus, even if the struts 120" extend along an entire length of the body 102", as shown in FIGS. 6-7, the body 102" may be expanded and/or compressed, as desired, to fit a target space of the bone. Similarly to the devices 100, 100' described above, a fixation element may be inserted between adjacent struts 120" to attach a fixation plate or other attachment thereto. Although the struts 120" are shown as extending along an entire length of the body 102", however, the struts 120" may be interrupted along a length of the body, similarly to the device 100'.

According to an exemplary method, the channel 108 of the graft containment device 100 may be filled with graft material via the first and/or second ends 104, 106 prior to positioning the graft containment device 108 in a target space or gap of a target bone—particularly, the mandible. As described above, the space or gap may be between two separated portions of bone so that the graft containment device 100 acts as a bridge to connect the two separated portions. Alternatively, the graft containment device 100 may be positioned within a space at an end of the bone so that only one end of the graft containment device 100 contacts the bone or within a recess formed within the bone so that the graft containment device 100 contacts the bone along three sides thereof. Although the exemplary method below describes using the graft containment device 100 to fill a space between separated portions of bone, it will be understood by those of skill in the art that the graft containment device 100 may be used to fill any of a variety of spaces or gaps formed in the bone. The graft containment device 100 may be expanded (i.e., increased in length by drawing the first and second ends 104, 106 farther away from one another so that the space 112 between adjacent turns of the one more helical structures 110 is increased), compressed (i.e., decreased in length by moving the first and second ends 104, 106 toward one another so that the space 112 between adjacent turns of the one or more helical structures 110 is decreased) and/or curved (i.e., bent along the longitudinal axis thereof) to fit the target space of the bone, as desired. As described above, where the longitudinal struts 120 extend along an entire length of the body 102, the graft containment device 100 may only be bent or curved to fit the target space. Where a length of the body 102 of the graft containment device 100 is too long for the target space, a surgeon or other user may cut the body 102 to the desired length. Longitudinal struts 120' that are interrupted along a length of the graft containment device 100', however, may additionally be expanded and/or compressed to fit the target space. Similarly, struts 120" that have an oscillating wave configuration may also be expanded, compressed and/or curved, as desired.

Once the graft containment device 100 has been positioned in the target space, as desired, additional graft material may be packed into the channel 108 via the spaces 112 between adjacent helical turns of the one or more helical structures 110. The graft containment device 100 may then be fixed to the bone via a fixation plate 150 or other attachment, which may form a bridge between and/or align separated portions of the bone. The fixation plate 150 may be positioned along the length of the graft containment device 100 so that openings 154 extending through the fixation plate 150 are substantially aligned with the longitudinal struts 120. First and second ends 156, 158 of the fixation plate 150 may extend beyond first and second ends 104, 106 of the graft containment device 100, respectively, so that the first and second ends 156, 158 of the fixation plate 150 extend over the separated portions of bone permitting the plate 150 to be fixed to both the graft containment device 100 and the separated portions of bone. In particular, fixation elements 152 may be inserted through the openings 154 of the fixation plate 150 and through the space 122 between adjacent longitudinal struts 120 to fix the fixation plate 150 the graft containment device 100. Fixation elements 152 may be similarly inserted through openings 154 along portions of the fixation plate extending over the bone to fix the fixation plate 150 thereto. Although the exemplary method above describes the positioning and use of the graft containment device 100, it will be understood by those of skill in the art that the devices 100' and 100" may be similarly positioned and utilized.

Figure 9:
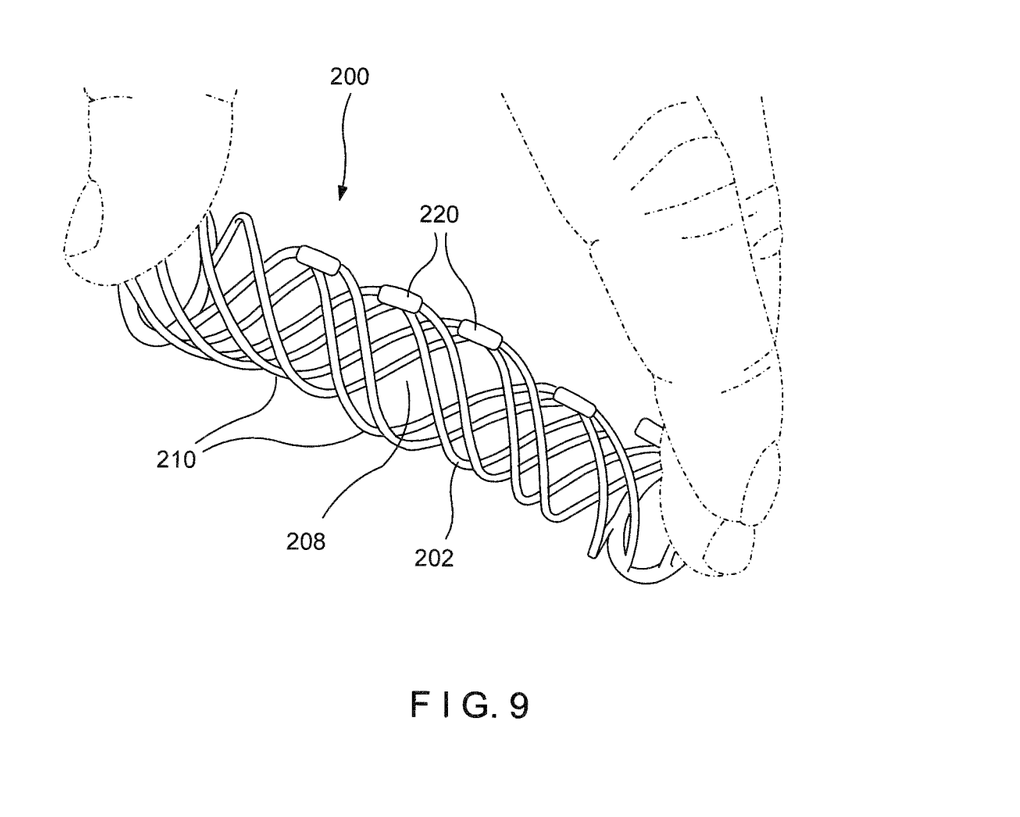
FIG. 9 shows a perspective view of the device of FIG. 6, in an expanded configuration.
Figure 10:
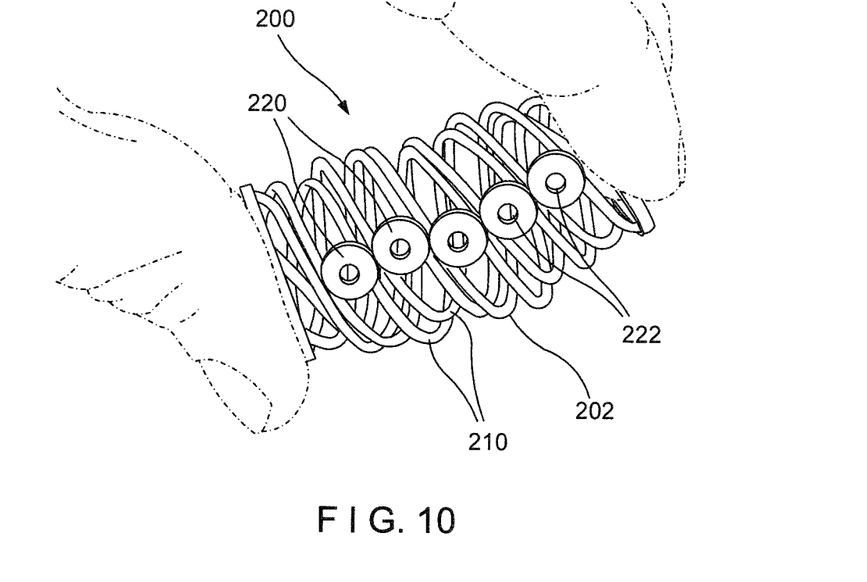
FIG. 10 shows a perspective view of the device of FIG. 6, in a compressed configuration.
Figure 11:
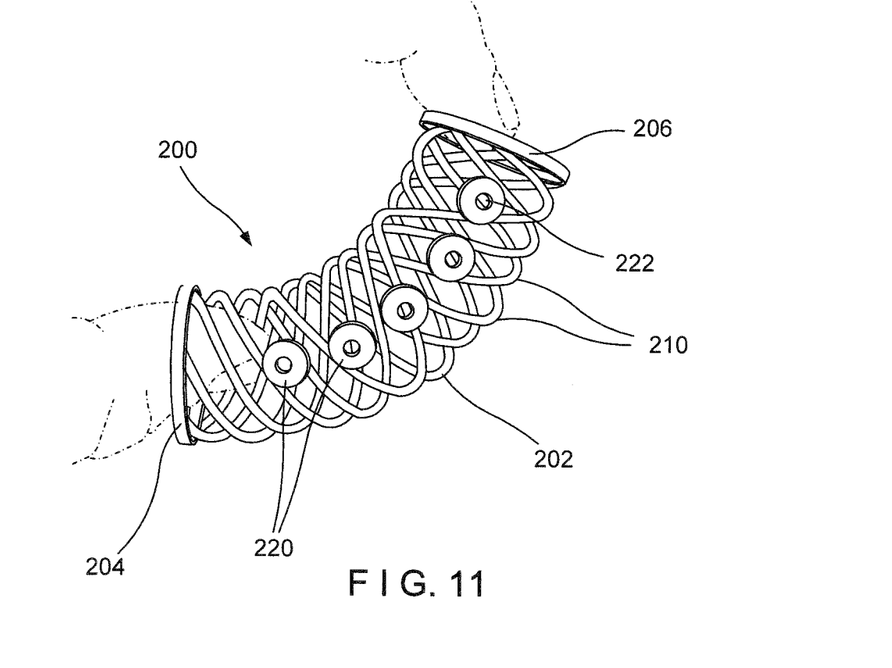
FIG. 11 shows a perspective view of the device of FIG. 6, in a curved configuration.

As shown in FIGS. 8-11, a graft containment device 200 may be substantially similar to the device 100, as described above, comprising a body 202 formed via one or more helical structures 210 extending from a first end 204 to a second end 206 to define a channel 208 extending longitudinally therethrough. The body 202 may be substantially similar to the body 102 described above with respect to the device 100. Rather than longitudinal struts, however, the graft containment device 200 may include a plurality of buttons 220, each button 220 connecting adjacent turns of the one or more helical structures 210. One or more of the buttons 220 may includes an opening 222 extending therethrough for receiving a shaft of a bone fixation element such as, for example, a bone screw, so that a fixation plate or other attachment may be fixed to the graft containment device 200. Each of the plurality of buttons 120 may be separated from one another along a length of the body 202. For example, the buttons 220 may be alternatingly positioned between adjacent turns of the helical structures 210. The graft containment device 200, however, may include any number of buttons 220, each of the buttons 220 spaced from one another at any desired distance along a length of the body 202. The spacing between adjacent buttons 220 permits the graft containment device 200 to be expanded (as shown in FIG. 9), compressed (as shown in FIG. 10) and/or bent (as shown in FIG. 11) to fill a target space within or between separated portions of a target bone. The graft containment device 200 may be used in a manner substantially similar to the device 100, as described above.

Although the graft containment devices 100, 200 are shown as having one or more helical structures extending along a length thereof in a single direction about a longitudinal axis of the devices 100, 200, it will be understood by those of skill in the art that a graft containment device according to the present invention may, alternatively, comprise helical structures extending about a longitudinal axis thereof in opposing directions. A first helical structure may extend about the longitudinal axis in a first direction while a second helical structure may extend about the longitudinal axis in a second direction opposite the first direction.

Figure 12:
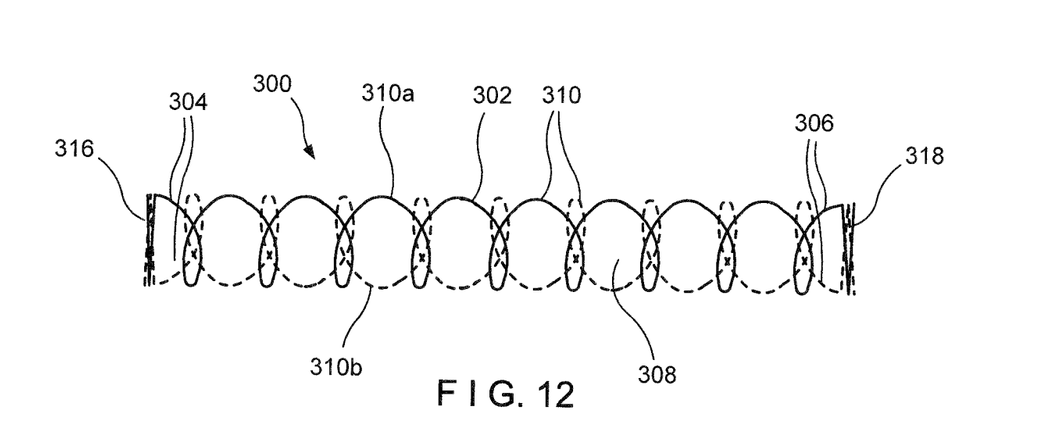
FIG. 12 shows a longitudinal side view of a device according to another exemplary embodiment of the present invention.
Figure 13:
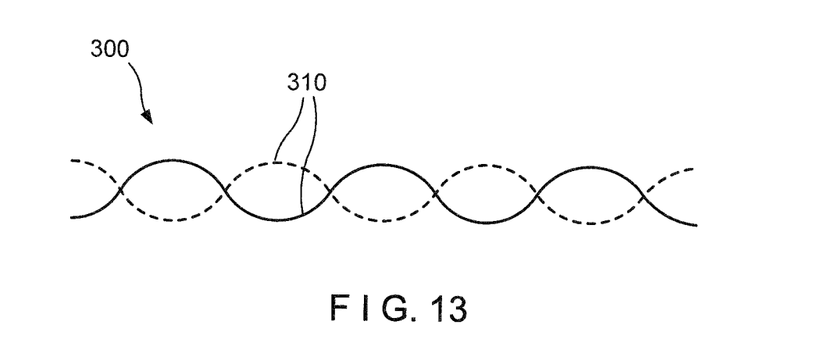
FIG. 13 shows an expanded longitudinal side view of the device according to FIG. 10, where crossing points of helical structures are not connected.
Figure 14:
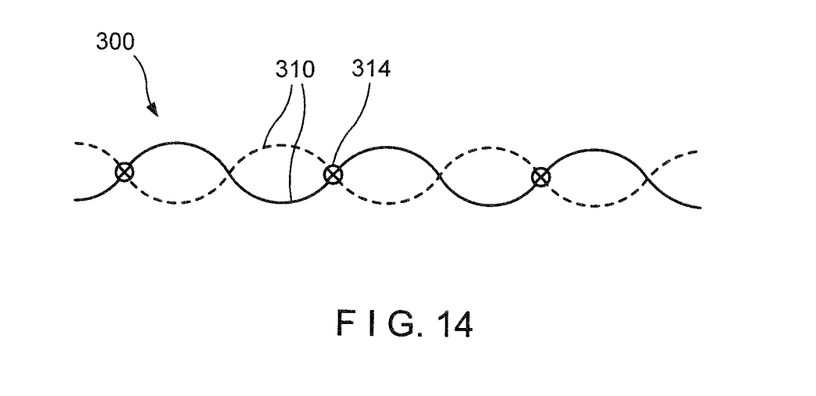
FIG. 14 shows an expanded longitudinal side view of the device according to FIG. 10, where crossing points of helical structures are connected.

For example, as shown in FIGS. 12-14, a graft containment device 300 may be substantially similar to the devices 100, 200 described above, comprising a body 302 formed via helical structures 310 extending from a first end 304 to a second end 306 to define a channel 308. A first helical structure 310*a*, however, extends about a longitudinal axis of the body 302 in a first direction while a second helical structure 310*b* extends about the longitudinal axis in a second direction opposite the first direction B i.e., the angles of the helices of the first and second structures 310, 320 are inclined to form a V-like shape where they cross. Similarly to the devices 100, 200, first ends 304 of the helical structures 310 may be connected to one another via a first connecting structure 316, which may be configured as, for example, a ring. Second ends 306 of the helical structures 310 may be connected to one another via a second connecting structure 318, which may be configured as, for example, a ring. Although the graft containment device 300 is shown and described as being comprised of two helical structures 310, it will be understood by those of skill in the art that the graft containment device 300 may include more than two helical structures 310, if so desired, so long as at least two of the helical structures 310 along the length of the body 302 in opposing directions.

In one exemplary embodiment, as shown in FIG. 13, the multiple helical structures 310 extend freely so that the helical structures 310 are not connected to one another except via the first and second connecting structures 316, 318 at the first and second ends 304, 306, respectively. In another exemplary embodiment, as shown in FIG. 14, the helical structures 310 may be connected to one another at one or more points 314 where the first and second helical structures 310a, 310b cross one another. The helical structures 310 may be connected at every crossing point 314 or, alternatively, may be connected at specific crossing points 314, as desired.

Although not shown, it will be understood by those of skill in the art that the graft containment device 300 may also include structures or features for receiving fixation elements such as, for example, the longitudinal struts 120 described above in regard to the device 100 or the buttons 220 described above in regard to the device 200. In one exemplary embodiment, the buttons 220 may act as a connection at crossing points 314.

Figure 15:
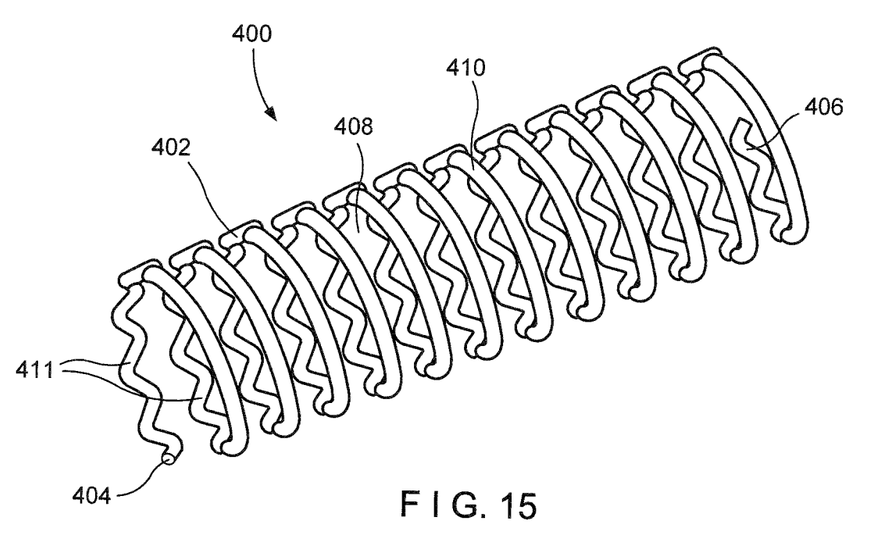
FIG. 15 shows a perspective view of a device according to yet another exemplary embodiment of the present invention.
Figure 16:
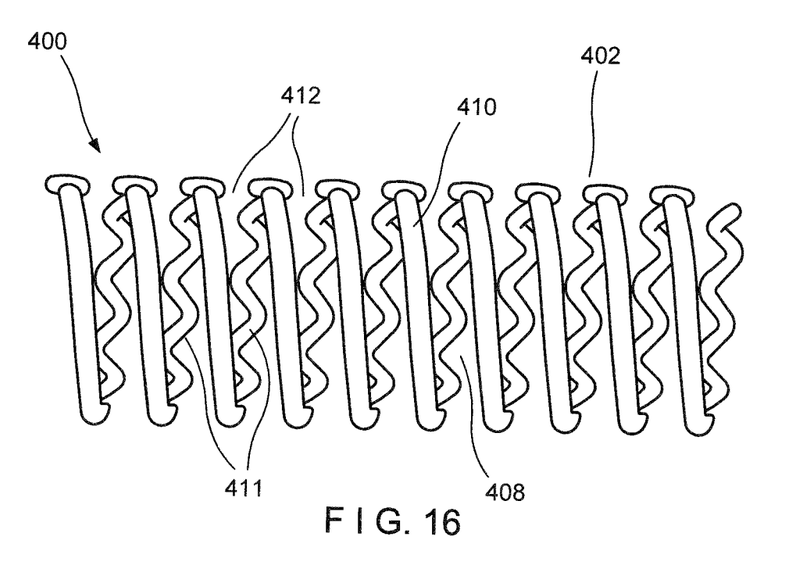
FIG. 16 shows an enlarged longitudinal top view of the device of FIG. 13.

As shown in FIGS. 15-16, a device 400 according to another exemplary embodiment of the present invention may be substantially similar to the devices 100-300 described above, comprising a body 404 formed via a helical structure 410 extending from a first end 404 to a second end 406 to define a channel 408. The helical structure 410, however, may include portions which have a wave configuration 411. The wave configuration 411 may extend along portions of the helical structure 410 along one side of the body 402. Alternatively, the wave configuration 411 may extend along the entire helical structure 410.

The wave configuration 411 may provide greater retention for graft material received within the channel 408. In addition, the wave configuration 411 may interlock with one another when the graft containment device 400 is compressed, providing rigidity to the graft containment device 400. The helical structure 410 is configured so that, even when portions of the wave configuration are interlocked, graft material may be packed into the channel 408 via a space 412 between adjacent turns of the helical structure 410 by moving the adjacent turns away from one another to increase the space 412 therebetween.

It will be understood by those of skill in the art that various modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A bone graft containment device, comprising:
a body formed via one or more helical structures extending about a longitudinal axis of the body from a first end to a second end to define a channel extending longitudinally through the body, wherein each of the one or more helical structures of the body forms a helix surrounding the channel, the channel configured to receive a bone graft material therein, each of the one or more helical structures formed of a material permitting the body to be one of expanded, compressed and curved to fill a target space of a target bone;
a first fixation element receiving structure connecting at least two adjacent turns of the one or more helical structures, wherein the first fixation element receiving structures is a first button connecting adjacent turns of the one or more helical structures and including an opening extending therethrough for receiving a shaft of a fixation element; and
a second fixation element receiving structure including a second button separated from the first button via a distance along a length of the body.

2. The device of claim 1, further comprising a plurality of longitudinal struts extending along at least a portion of a length of the body, wherein the first fixation element receiving structure is formed by adjacent ones of the longitudinal struts, a spacing between the adjacent longitudinal struts being configured to receive a shaft of a fixation element.

3. The device of claim 2, wherein at least a first one of the longitudinal struts is interrupted along the length of the body so that the first longitudinal strut is divided into multiple longitudinal strut segments along the length of the body.

4. The device of claim 2, wherein the longitudinal struts extend along the length of the body in one of a linear configuration and an oscillating wave configuration.

5. The device of claim 1, wherein the body is formed via at least two helical structures.

6. The device of claim 5, further comprising a first connecting structure connecting the first end of the at least two helical structures and a second connecting structure connecting the second end of the at least two helical structures.

7. The device of claim 5, wherein a first one of the at least two helical structures extends in a first direction about the longitudinal axis of the body and a second one of the at least two helical structures extends in a second direction about the longitudinal axis of the body, the second direction opposing the first direction.

8. The device of claim 7, wherein the first and second helical structures are connected to one another at a point where the first and second helical structures cross one another.

9. The device of claim 1, wherein the one or more helical structures have a wave configuration along at least a portion of a length thereof so that, when the body is compressed, the wave configuration of adjacent turns of the one or more helical structures interlock with one another.

10. The device of claim 9, wherein the wave configuration extends along one side of the body.

11. The device of claim 1, wherein the one or more helical structures define a substantially cylindrical shape.

12. The device of claim 1, wherein the one or more helical structures extend about the longitudinal axis at an angle relative to planes perpendicular to the longitudinal axis so that a shape of the body matches a shape of the target space to be filled.

13. The device of claim 1, wherein the second fixation element receiving structure connects at least two adjacent turns of the one or more helical structures.

14. The device of claim 1, wherein the body is flexed and deformed to match the exact shape of the target space.

15. A bone graft system, comprising:
a graft containment device including a body formed via one or more helical structures extending about a longitudinal axis of the body from a first end to a second end to define a channel extending longitudinally through the body, wherein each of the one or more helical structures of the body forms a helix surrounding the channel, the channel configured to receive a bone graft material therein, each of the one or more helical structures formed of a material permitting the body to be one of expanded, compressed and curved to fill a target space of a target bone
a fixation plate sized and shaped to be positioned along a length of the graft containment device to attach the graft containment device to the bone, the fixation plate including openings extending therethrough for receiving fixation elements therethrough; and
a plurality of longitudinal struts extending along at least a portion of a length of the body, a spacing between adjacent ones of the longitudinal struts forming a plurality of fixation element receiving structures connecting at least two adjacent turns of the one or more helical structures, each fixation element receiving structure being configured to receive a shaft of a fixation element therein.

16. The system of claim 15, wherein a first helical structure of the one or more helical structures extends in a first direction about the longitudinal axis of the body and a second helical structure extends in a second direction about the longitudinal axis of the body, the second direction opposing the first direction.

17. The system of claim 15, wherein the one or more helical structures have a wave configuration along at least a portion of a length thereof so that, when the body is compressed, the wave configuration of adjacent turns of the one or more helical structures interlock with one another.

18. A bone graft system, comprising:
a graft containment device including a body formed via a first helical structure extending about a longitudinal axis of the body from a first end to a second end to define a channel extending longitudinally through the body, wherein the first helical structure forms a helix surrounding the channel, the channel configured to receive a bone graft material therein, the first helical structure being formed of a material permitting the body to be one of expanded, compressed and curved to fill a target space of a target bone, wherein the graft containment device further includes a first fixation element receiving structure connecting at least two adjacent turns of the first helical structure; and
a fixation plate sized and shaped to be positioned along a length of the graft containment device to attach the graft containment device to the bone, the fixation plate attachment including openings extending therethrough for receiving fixation elements therethrough.

19. The system of claim 18, further comprising a plurality of fixation element receiving structures, wherein the fixation element receiving structures are buttons, each button connecting adjacent turns of the first helical structure and including an opening extending therethrough for receiving a shaft of a fixation element, each button separated from an adjacent button via a distance along a length of the body.

20. The system of claim 18, wherein the graft containment device includes a second helical structure extending about the channel, the first helical structure extending in a first direction about the longitudinal axis of the body while the second helical structure extends in a second direction about the longitudinal axis of the body, the second direction opposing the first direction.

21. The system of claim 18, wherein the first helical structure has a wave configuration along at least a portion of a length thereof so that, when the body is compressed, the wave configuration of adjacent turns of the first helical structure interlock with one another.

22. The system of claim 18, further comprising a plurality of fixation element receiving structures, wherein the fixation element receiving structures are longitudinal struts extending along at least a portion of a length of the body, a spacing between adjacent longitudinal struts configured to receive a shaft of a fixation element.

23. The system of claim 18, wherein the graft containment device further includes a second fixation element receiving structure connecting at least two adjacent turns of a second helical structures.

* * * * *